United States Patent
Jung et al.

(10) Patent No.: US 11,439,601 B2
(45) Date of Patent: Sep. 13, 2022

(54) SOLID PREPARATION COMPOSITION FOR ORAL ADMINISTRATION OF COLONIC PURGATIVE CONTAINING ANHYDROUS SODIUM SULFATE, POTASSIUM SULFATE, ANHYDROUS MAGNESIUM SULFATE AND SIMETHICONE

(71) Applicant: PHARMBIO KOREA CO., LTD., Chungcheongbuk-do (KR)

(72) Inventors: Hyun Jung Jung, Seoul (KR); Zong Zhu Piao, Gyeonggi-do (KR); Kyung Su Lee, Gyeonggi-do (KR); Hwan Hyuk Lee, Gyeonggi-do (KR)

(73) Assignee: PHARMBIO KOREA CO., LTD., Chungcheongbuk-do (KR)

( * ) Notice: Subject to any disclaimer, the term of this patent is extended or adjusted under 35 U.S.C. 154(b) by 0 days.

(21) Appl. No.: 17/251,864

(22) PCT Filed: May 27, 2019

(86) PCT No.: PCT/KR2019/006311
§ 371 (c)(1),
(2) Date: Dec. 14, 2020

(87) PCT Pub. No.: WO2019/245177
PCT Pub. Date: Dec. 26, 2019

(65) Prior Publication Data
US 2021/0251908 A1 Aug. 19, 2021

(30) Foreign Application Priority Data

Jun. 18, 2018 (KR) ........................ 10-2018-0069785

(51) Int. Cl.
| | |
|---|---|
| A61K 9/28 | (2006.01) |
| A61K 9/00 | (2006.01) |
| A61K 9/20 | (2006.01) |
| A61K 31/695 | (2006.01) |
| A61K 33/04 | (2006.01) |
| A61K 33/06 | (2006.01) |

(52) U.S. Cl.
CPC .......... *A61K 9/2853* (2013.01); *A61K 9/0053* (2013.01); *A61K 9/2013* (2013.01); *A61K 9/2027* (2013.01); *A61K 9/2095* (2013.01); *A61K 31/695* (2013.01); *A61K 33/04* (2013.01); *A61K 33/06* (2013.01)

(58) Field of Classification Search
CPC .................................................. A61K 31/695
See application file for complete search history.

(56) References Cited

U.S. PATENT DOCUMENTS

| | | |
|---|---|---|
| 5,922,351 A | 7/1999 | Daher |
| 6,946,149 B2 | 9/2005 | Cleveland |
| 2012/0265011 A1* | 10/2012 | Pelham ................ A61K 31/095 |
| | | 600/109 |

FOREIGN PATENT DOCUMENTS

| | | | | |
|---|---|---|---|---|
| EP | 2322190 B1 * | 4/2013 | ........... | A61K 9/0095 |
| KR | 10-2013-0048790 A | 5/2013 | | |
| KR | 10-2015-0089430 A | 8/2015 | | |
| KR | 10-2019-0041233 A | 4/2019 | | |
| WO | WO-2012/079118 A1 | 6/2012 | | |
| WO | WO-2013/059881 A1 | 5/2013 | | |

OTHER PUBLICATIONS

Sudduth, Gastrointestinal Endoscopy, 42, 5, 1995 (Year: 1995).*
International Search Report from corresponding PCT Application No. PCT/KR2018/006311, dated Aug. 28, 2019.
Johnson, D. A., et al.; "Optimizing Adequacy of Bowel Cleansing for Colonoscopy: Recommendations From the US Multi-Society Task Force on Colorectal Cancer", Gastroenterology 2014;147: 903-924.
Lopes, T., et al.; "Efficacy and tolerability of suprep with and without simethicone for routine colonoscopy for colorectal cancer screening", Mercy Medical Center. Aug. 29, 2017, ClinicalTrials. gov identifier: NCT02523911, inner pp. 1-5.
Extended European Search Report from corresponding European Patent Application No. 19822417.2, dated Aug. 9, 2021.
Drug Approval Data SUPREP, "https://www.accessdata.fda.gov/drugsatfda_docs/nda/2010/022372_suprep_toc.cfm", 2011, pp. 1-2.

* cited by examiner

*Primary Examiner* — Robert A Wax
*Assistant Examiner* — William Craigo
(74) *Attorney, Agent, or Firm* — Harness, Dickey & Pierce, P.L.C.

(57) ABSTRACT

The present invention relates to a solid colonic purgative for oral application, containing anhydrous magnesium sulfate, potassium sulfate, anhydrous sodium sulfate, and, additionally, simethicone. The present invention is more satisfactory in the colon cleansing effect even with the doses reduced by up to about 20 percent compared to those of a conventional colonic purgative consisting of anhydrous magnesium sulfate, potassium sulfate and anhydrous sodium sulfate. Besides, the present invention, due to the reduced doses, has less unpleasant taste or odor caused by the main ingredients and requires a less intake of the preparation and water, improving drug compliance significantly. Further, unlike the conventional solid colonic purgative, the present invention can be prepared into tablets without using a water-soluble lubricant. In other words, the present invention can be formulated into a solid preparation for oral application by using a water-soluble lubricant, or even without using any water-soluble lubricant.

3 Claims, No Drawings

SOLID PREPARATION COMPOSITION FOR ORAL ADMINISTRATION OF COLONIC PURGATIVE CONTAINING ANHYDROUS SODIUM SULFATE, POTASSIUM SULFATE, ANHYDROUS MAGNESIUM SULFATE AND SIMETHICONE

CROSS-REFERENCE TO RELATED APPLICATIONS

This application is a national phase application of PCT Application No. PCT/KR2019/006311, filed on May 27, 2019, which claims benefit of Korean Patent Application 10-2018-0069785, filed on Jun. 18, 2018. The entire disclosure of the applications identified in this paragraph are incorporated herein by references.

FIELD

The present invention relates to a solid preparation composition for oral application of colonic purgatives containing anhydrous sodium sulfate, potassium sulfate and anhydrous magnesium sulfate as main ingredients, and, additionally, simethicone, and a solid formulation of a hitherto unprecedented new drug.

BACKGROUND

Colon cleanse is completely clearing the colon (also called the large bowel or large intestine) of fecal debris without damaging colonic mucosa or blood vessels in order to view the clear appearance of the colonic mucosa removed of fecal debris. The existing colon cleansers are largely divided into osmotic agents and stimulants.

An example of osmotic agents is polyethylene glycol (PEG) solution. PEG, having little effect on the amount of plasma and electrolytes, is suitable for patients with comorbid diseases, including renal diseases, cardiac diseases, and liver diseases. Yet, the PEG solution is associated with poor compliance, which is attributed to the repulsive taste and large dose of 4 liters that patients are supposed to consume. Some osmotic products use a combination of PEG and ascorbic acid to make a colon cleansing effect with a reduced dose of 2 liters, but still have an offensive taste peculiar to PEG, which renders the dose unbearable for the patients.

The stimulant laxative includes, for example, sodium picosulfate hydrate, magnesium oxide, and citric acid complex. When used in adults, it is generally taken as two doses on the day before the colonoscopy, with the first dose of 170 ml taken at 8 a.m. or earlier and the second dose of 170 ml taken 6-8 hours later. The dose is significantly reduced compared with that of the PEG preparation. But, the medication compliance is not that high, since it is recommended to drink 250 ml drinks of water per hour after taking the second dose in order to prevent dehydration.

The present invention is a colon cleanser preparation based on a hyperosmotic agent containing anhydrous sodium sulfate, potassium sulfate, anhydrous magnesium sulfate, and simethicone. The hyperosmotic agent is advantageous over the isotonic osmotic agent in that a small amount of liquid is consumed.

According to Korean Patent Laid-Open Publication No. 10-2015-0089430, bowel preparations composed of three sulfates such as magnesium sulfate, potassium sulfate, and sodium sulfate are reported to be very safe and effective and have triggered the development of a new product such as Suprep Bowel Prep Kit in the United States. Such preparations consisting of the three sulfates are also commercially available in South Korea with the brand name of SUPREP, SUCLEAR, and so on.

Although the exact mechanism of action of simethicone is not yet clear, simethicone is a drug that inhibits the production of intestinal gas bubbles and is thus widely used as an adjunctive agent for bowel preparation. Adding simethicone after administration of PEG effectively is reported to reduce the intestinal gas bubbles and increase the colon cleansing effect.

SUMMARY

Technical Problem

It is reported that inadequate colon cleanse prolongs the procedural time for endoscope insertion, increases the patient's discomfort, and furthermore, reduces the colon lesion detection rates. Adequate colon cleanse is hence essential for successful colonoscopy. In addition, the inventors of the present invention have considered that there is a demand for a colon cleanser designed not only to secure an adequate colon cleanse for successful colonoscopy but also to relieve discomfort caused in the procedure of colon cleanse by reducing the dose of the liquid medications the patient have to consume.

According to Korean Patent Laid-Open Publication No. 10-2017-0132565, colon cleansers are developed preferably in the tablet form, since liquid preparations are associated with poor medication compliance attributed to the salty taste and offensive odor peculiar to sulfates, and an excess of sweeteners, flavors, or the like often used to remove the strong stench of sulfates, similar to that of a rotten egg, has only a limited effect.

Unfortunately, some problems may occur during tablet manufacturing. The first problem is capping and lamination, which happen when the upper segment of a tablet separates from the main body of the tablet and comes off as a cap, or a tablet splits apart into horizontal layers to leave horizontal lines or peel off the layers.

The second is sticking, which occurs when powder from the formulation attaches and sticks to the punch faces, resulting in defective surfaces of the tablet. The sticking defect is divided into chipping (the breaking of the round edges of a tablet with cracks or chips caused by expansion during a release of the tableting pressure) and picking (having a severe friction between the die wall and the surface of the tablet).

A remedy for these tableting defects is increasing the amount of the lubricants.

Lubricants, also called glidants, are substances used to provide slipperiness and reduce frictions in the manufacture of tablets or preparations for cutaneous application.

The types of lubricants include aliphatic esters (e.g., glyceryl behenate, glyceryl palm itostearate, glyceryl monostearate, glyceryl trim iristearate, glyceryl tristearate, or sucrose aliphatic ester), fatty acids and alcohols (e.g., palmitic acid, palmitoyl alcohol, stearic acid, or stearyl alcohol), oils (e.g., hydrogenated castor oils, mineral oils, or hydrogenated vegetable oils), and so on.

As can be seen from the above representative examples, the lubricants are mostly hydrophobic, derived from fatty acids and alcohols, and hence insoluble to water. If tablets containing such lubricants are used as a colonic purgative, the lubricants insoluble to water in the colon may obstruct the endoscopic visualization of the colon.

Water-soluble lubricants, although commercially available as sodium lauryl sulfate or polyethylene glycol, require a higher concentration than any other existing lubricant when in use, and furthermore, can hardly realize satisfactory lubrication. With a lack of the lubrication, tableting defects, such as capping, sticking, or lamination, may occur during the compression (tableting) process.

Accordingly, it is an object of the present invention to provide a solid preparation composition for oral application of a colonic purgative that includes anhydrous sodium sulfate, potassium sulfate, anhydrous magnesium sulfate, and simethicone, thereby improving medication compliance. It is another object of the present invention to provide such a solid preparation composition for oral application of a colonic purgative and increase productivity by direct tableting even without adding a lubricant.

Technical Solution

The aforementioned objects of the present invention are achieved by the means of the present invention as follows:

(1) A composition, which is a solid preparation composition for oral application of a colonic purgative, comprising anhydrous magnesium sulfate, potassium sulfate, anhydrous sodium sulfate, and simethicone, wherein the composition can be manufactured into a preparation without adding a lubricant;

(2) The composition of (1), wherein water is added in an amount of 0.1 to 2.0 wt. % with respect to the total weight of an uncoated tablet in the manufacture of the preparation;

(3) The composition of (1) or (2), further comprising a water-soluble binder;

(4) The composition of (3), wherein the water-soluble binder is at least one selected from the group consisting of copovidone, polyethylene glycol, and povidone;

(5) The composition of any one of (1) to (4), further comprising a water-soluble coating agent;

(6) The composition of (5), wherein the water-soluble coating agent is at least one selected from the group consisting of polyvinyl alcohol-polyethylene glycol graft copolymer, aminomethacrylate copolymer, and methyl methacrylate copolymer; and (7) A solid preparation for oral application being manufactured by direct tableting using the composition of (1) to (4).

Effects of Invention

The present invention converts the dosage form of the conventional liquid preparation into tablets to mask a nasty odor and an unpleasant taste peculiar to sulfates during administration.

In addition, according to one embodiment of the present invention implemented as a tablet, it is possible to exclude the use of a lubricant in the tablet, securing the endoscopic visualization of colon for colonoscopy and reducing bitter taste and offensive odor to improve medication compliance.

Particularly, the present invention provides a remedy for the tableting defects possibly occurring during tablet manufacturing and renders the compression (tableting) process successful.

DETAILED DESCRIPTION

The present invention is directed to a new drug preparation using new materials as main ingredients in a colonic purgative. The present invention is also directed to a solid preparation composition for oral application of a colonic purgative that comprises hitherto unprecedented main ingredients such as anhydrous sodium sulfate, potassium sulfate, anhydrous magnesium sulfate, and simethicone, to improve medication compliance.

Sulfate preparations are drugs that provide sulfate anions, which are poorly absorbed into the human body, and induce excess water retention in the gastrointestinal (GI) tract with the osmotic effect of the cations related to the unabsorbed sulfate anions, thereby causing severe watery diarrhea.

Korean Patent Laid-Open Publication No. 10-2013-0048790 specifies the effectiveness of two osmotic laxatives, sodium sulfate and magnesium sulfate. However, these osmotic laxatives can cause changes in electrolytes and metabolism, such as hypermagnesemia, hypochloremia, hypokalemia, and low serum osmotic pressure, along with diarrhea. For this reason, sulfate preparations generally include a composite of three drugs, which is a combination of anhydrous magnesium sulfate, potassium sulfate, and anhydrous sodium sulfate.

It is approved that the colonic purgative using anhydrous magnesium sulfate, potassium sulfate, and anhydrous sodium sulfate can be formulated into a liquid preparation, which is commercially available. One bottle (6 oz) of the liquid preparation contains 1.6 g of anhydrous magnesium sulfate, 3.13 g of potassium sulfate, 17.5 g of anhydrous sodium sulfate, a sweetener, and a preservative. According to a clinical test, the preparation consisting of the three sulfates has higher colon cleansing performance and less side effects than the PEG-based preparation. The preparation has received favorable reviews because of its reduced dose compared with the PEG-based preparation.

Yet, the preparation consisting of the three sulfates is all the same as the PEG-based preparation from the patients' point of view in that it requires patients to take a huge dose of drugs and tolerate a significant discomfort of medication attributed to the bitter taste characteristic of the sulfates. Besides, the patients are bound to produce diarrhea by taking the medication and hence have to drink plenty of water adequately before, during, and after taking the medication.

For a new approach to solving this problem, many attempts have been made to convert the liquid preparations into powders or to develop tablet preparations as disclosed in Korean Patent Laid-Open Publication No. 10-2015-0089430. Even if preparations are implanted in a tablet dosage form, they can be improved somewhat by a slight reduction of the bitter taste peculiar to sulfates, but still need to overcome the limitations associated with a huge dose of medication, such as taking a large quantity of tablets and having to drink plenty of water for the ingestion of such a large quantity of tablets and the reduction of side effects caused by diarrhea or the like.

Surprisingly, the dose of a preparation using anhydrous magnesium sulfate, potassium sulfate, and anhydrous sodium sulfate in combination with simethicone is found out to be less by about 20% than that of the conventional preparation using anhydrous magnesium sulfate, potassium sulfate, and anhydrous sodium sulfate as approved in South Korea. In other words, the present invention may have the same level of colon cleansing effect as the conventional preparation, for example, with doses as low as 80%, 85-95%, or 90% of those of the mentioned conventional preparation.

Although the exact mechanism of action of simethicone is not yet clear, simethicone is considered as a drug that inhibits the production of intestinal gas bubbles and is thus used to eliminate intestinal gas bubbles possibly generated during the use of a PEG-based colonic purgative, and additionally, to improve endoscopic visualization of colon during colonoscopy.

Known as a drug used in the practice of colonoscopy, simethicone is not taken as a drug like bisacodyl or magnesium citrate that plays a direct role in the colon cleanse by increasing the bowel movement, but considered to be used just for the removal of intestinal gas bubbles when the colonic purgative is causing production of gas bubbles.

The guidelines for medication issued in the United States in 2014 do not recommend using adjunctive agents, such as intestinal movement enhancers including bisacodyl or magnesium citrate. In addition, simethicone is not recommended for routine use.

The inventors of the present invention have found it out by accident that using anhydrous magnesium sulfate, potassium sulfate, and anhydrous sodium sulfate in combination with simethicone create a synergy to make the same level of colon cleansing effect even with reduced doses of anhydrous magnesium sulfate, potassium sulfate, and anhydrous sodium sulfate, the exact mechanism of which is not yet known.

The present invention is, therefore, directed to a new drug using anhydrous magnesium sulfate, potassium sulfate, anhydrous sodium sulfate, and simethicone as main ingredients.

The present invention may be implemented into liquid preparations, or solid preparations such as powders or tablets for masking the unpleasant taste peculiar to sulfates. Particularly, the present invention is directed to a solid preparation for oral application, including powders or tablets.

When the present invention is embodied into tablets, for example, one tablet may contain 102.86 mg of anhydrous magnesium sulfate, 201.07 mg of potassium sulfate, 1125.00 mg of anhydrous sodium sulfate, and 11.43 mg of simethicone. According to the medication instruction, there are two doses: the first dose of 14 tablets taken with 1275 ml of water within one hour the day before the colonoscopy, and the second dose of 14 tablets with 1275 ml of water within one hour in the morning on the day of the colonoscopy, which doses are no more than 90% of those of the conventional preparation. For reducing the doses to 80% of those of the conventional preparation, it has only to reduce the doses of the main ingredients and the amount of water proportionately.

According to an embodiment of the present invention, the tablets may be prepared by mixing anhydrous magnesium sulfate, potassium sulfate, anhydrous sodium sulfate, and simethicone, adjusting the content of water as necessary, adding a binder, and then tableting the mixture.

As necessary, a coating is applied to the surface of the uncoated tablets to further mask the bitter taste of the main ingredients.

The tablet of the present invention includes a water-soluble binder. The water-soluble binder may be a combination of ingredients disclosed in the Pharmaceutical Excipients Handbook. For example, the water-soluble binder may be at least one selected from the group consisting of copovidone, polyethylene glycol, and povidone. The present invention, which consists of water and a water-soluble binder, does not form a buildup of residual debris in the intestines, securing definite visualization of colon for the practice of colonoscopy conducted after administration of the drug of the present invention.

In an embodiment of the present invention, it is characterized by including copovidone as a water-soluble binder. Copovidone, soluble to water, does not leave any residual debris or crystals in the intestines. The content of the water-soluble binder may be adjusted appropriately by those skilled in the art.

The conventional colonic purgative including sulfates as main ingredients necessarily uses lubricants when formulated into a solid preparation for oral application. Korean Patent Laid-Open Publication No. 10-2015-0089430, for example, discloses a solid preparation for oral application that includes magnesium sulfate, potassium sulfate, and sodium sulfate as active ingredients, polyethylene glycol as an excipient, and sodium stearyl fumarate as a lubricant.

In fact, the lubricant, having a relatively high turbidity, obstructs colon cleanness. The reason for necessarily using a lubricant in the manufacture of the conventional solid preparation for oral application is that successful tableting is difficult without a lubricant. Specifically, when ingredient materials are simply formulated into tablets without adding any lubricant, they attach to the tableting machine to cause process defects, such as sticking. It may lead to unsuccessful tableting or poor quality uniformity. Hence, the addition of a lubricant is inevitably essential.

On the other hand, the inventors of the present invention have surprisingly found it out that a hitherto unprecedented new drug containing anhydrous magnesium sulfate, potassium sulfate, anhydrous sodium sulfate, and simethicone as main ingredients can be formulated into a solid preparation for oral application without any process defects even when the use of a lubricant is excluded. Though the exact mechanism is unknown, it is presumable that the combination of the main ingredients of the hitherto unprecedented new drug, i.e., anhydrous magnesium sulfate, potassium sulfate, anhydrous sodium sulfate, and simethicone, generates an unknown synergy to overcome process defects without using any lubricant.

The present invention is therefore characterized in that a lubricant may be either included or excluded. In other words, the present invention can be formulated into a solid preparation for oral application even without a lubricant and thus control the occurrence of turbidity caused by a lubricant, further improving the colon cleanness.

In an embodiment of the present invention, it is characterized in that the water content is maintained at a defined level in the process of formulation into a solid preparation for oral application as necessary. Specifically, the present invention is characterized by adding 0.1 to 2.0 wt. % of water with respect to the total weight of the uncoated tablet in the formulation process. Preferably, 0.5 to 1.0 wt. % of water is used with respect to the total weight of the uncoated tablet, and it contributes to the best productivity.

Even if containing 0.1 to 2.0 wt. % of water with respect to the total weight of the uncoated tablet, the new drug of the present invention including simethicone realizes a reduction of its doses to be lower than the doses of the conventional sulfate preparation as described above while retaining its function as a colonic purgative, and more improves process defects in the manufacture of the solid preparation for oral application. That is, the solid preparation for oral application can be manufactured without a lubricant, and furthermore, the water content in the above-defined range secures better advantages for the process.

In the manufacture of a solid preparation for oral application through granulation and tableting, it is general to employ wet granulation rather than dry granulation so that the formed granules contain water. Generally, no water is added in the case of simply mixing ingredients and conducting a direct tableting without granulation. The reason lies in that with some water, certain ingredients may show adhesion to cause defects in the tableting process.

In an embodiment of the present invention, however, it is characterized by containing water even when a solid preparation for oral application is manufactured by direct tableting. Unlike the conventional conception, the composition of the present invention can secure high process productivity without a lubricant, yet it has better advantages for the process especially when a defined amount of water is added prior to the direct tableting process.

In an embodiment of the present invention, it is characterized by performing a direct tableting to manufacture a solid preparation for oral application. That is, the present invention may be implemented into powders or tablets, and the ingredients are to be mixed together for the manufacture of powders or tablets. In mixing the ingredients, the ingredients are formed into granules through granulation or simply mixed together. The granulation for forming granules may be either dry granulation or wet granulation.

In an embodiment of the present invention, it is characterized in that in the above preparation process, the ingredients are simply mixed together and then subjected to direct tableting to form a solid preparation for oral application. For example, a solid preparation for oral application can be manufactured by mixing main ingredients with a high-speed mixer, adding water to the mixture of the main ingredients as necessary, mixing a water-soluble binder with the above mixture, and conducting a direct tableting with a tableting machine. As such, it may be preferable in view of the production efficiency to manufacture the solid preparation by direct tableting.

In wet granulation using water or another suitable solvent, a drying process is conducted to volatilize the solvent. This process is not only time consuming but associated with applying a certain amount of heat, so it may affect the stability of the solid preparation. Therefore, the preparation method is designed as a direct tableting method to reduce the process and time.

The present invention may further include applying a coating to the uncoated tablets for improving the masking of a bitter taste of sulfates. There has been no attempt to apply a coating to the solid preparations for oral application, because the coating agent may affect the turbidity. Yet, the inventors of the present invention have confirmed that the uncoated tablets of the present invention do not inhibit the turbidity even if they are coated with a water-soluble coating agent.

The water-soluble coating agent is a component that does not dissolve in the mouth upon oral administration, but shows high solubility to water in the stomach. As a non-limiting example, the water-soluble coating agent is preferably at least one selected from the group consisting of polyvinyl alcohol-polyethylene glycol graft copolymer, amino methacrylate copolymer, and methyl methacrylate copolymer. The content of the water-soluble coating agent may be appropriately adjusted by those skilled in the art.

Hereinafter, the present invention will be described with reference to examples, which are given for illustrative purposes only and are not construed to limit the scope of the present invention.

Examples

Tablets were formulated to have the doses given as follows (unit: mg).

TABLE 1

| Ingredients | Purpose of mixing | Comparative Example 1 | Comparative Example 2 | Example 1 | Example 2 | Example 3 |
|---|---|---|---|---|---|---|
| Anhydrous sodium sulfate | Main ingredient | 1125.00 | 1125.00 | 1125.00 | 1125.00 | 1125.00 |
| Potassium sulfate | Main ingredient | 201.07 | 201.07 | 201.07 | 201.07 | 201.07 |
| Anhydrous magnesium sulfate | Main ingredient | 102.86 | 102.86 | 102.86 | 102.86 | 102.86 |
| Simethicone | Main ingredient | — | — | 11.43 | 11.43 | 11.43 |
| Copovidone | Binder | 1-5 wt. % with respect to uncoated tablet | 1-5 wt. % with respect to uncoated tablet | 1-5 wt. % with respect to uncoated tablet | 1-5 wt. % with respect to uncoated tablet | 1-5 wt. % with respect to uncoated tablet |
| Sodium benzoate | Lubricant | 1-3 wt. % with respect to uncoated tablet | — | — | — | — |
| Kollicoat ® IR | Film coating agent | 1-3 wt. % with respect to uncoated tablet | 1-3 wt. % with respect to uncoated tablet | 1-3 wt. % with respect to uncoated tablet | 1-3 wt. % with respect to uncoated tablet | 1-3 wt. % with respect to uncoated tablet |
| Purified water | Wetting agent | — | — | — | 10 | 20 |

The above composition was formulated into tablets according to the following procedures.

Step 1: Mix anhydrous magnesium sulfate, potassium sulfate and anhydrous sodium sulfate with a high-speed mixer.

Step 2: Mix simethicone (excepting Comparative Examples 1 and 2) into the mixture of the step 1 with a high-speed mixer.

Step 3: Add water to the mixture of the step 2.

Step 4: Mix copovidone and sodium benzoate (Comparative Example 1) into the mixture of the step 3 with a mixer.

Step 5: Tablet the mixture of the step 4 with a rotary tableting machine.

Step 6: Film-coat the uncoated tablets of the step 5 with a fan-coating machine.

Step 7: Package the coated tablets of the step 6.

A comparison of the preparations manufactured by the above procedures was made in regards to the following items associated with the compression (tableting) process.

TABLE 2

| Item | Comparative Example 1 | Comparative Example 2 | Example 1 | Example 2 | Example 3 |
|---|---|---|---|---|---|
| Sticking | − | +++ | + | − | − |
| Capping | − | +++ | + | − | − |
| Flowability (repose angle) | 30° | 38° | 32° | 29° | 30° |
| Disintegration (uncoated tablets) | 15-20 min | 15-20 min | 15-20 min | 15-20 min | 15-20 min |
| Disintegration (film-coated tablets) | 20-25 min | 20-25 min | 20-25 min | 20-25 min | 20-25 min |

+++: Very highly frequent
++: Highly frequent
+: Frequent (defects shown)
−: No defects In order to determine the effect of the presence of a lubricant, a comparison was made between the Comparative Examples 1 and 2, showing that the Comparative Example 1 containing a lubricant was superior in productivity to the Comparative Example 2 containing no lubricant. The Comparative Example 2 had sticking and capping defects and a relatively high angle of repose, which indicated low flowability.

Surprisingly, the Example 1 containing simethicone in addition to the main ingredients had less sticking and capping defects and higher flowability than the Comparative Example 2. This presumably resulted from the fact that the simethicone added as an oily component delivered a lubricant effect to the mixture in the mixing step.

A comparison between Examples 1 and 2 showed the effect of water. The Example 1 of the present invention, even though containing no water, was excellent in properties associated with sticking, capping, and flowability relative to the Comparative Example 2 and thus considered to be industrially feasible as much as required. Yet, just adding a small amount of water as in Example 2 increased flowability and reduced the capping defect.

A comparison of Examples 2 and 3 was made in regards to the process depending on the added amount of water. An excess of water caused no capping defect, but resulted in a little bit more sticking defect (yet, less than in the Comparative Example 2). The appropriate water content is 0.1-2.0 wt. % per tablet, preferably 0.5-1.0 wt. % per tablet, for better productivity.

In addition, there was no difference in the disintegration time between the Comparative Examples and the Examples.

What is claimed is:

1. A tablet for oral application of a colonic purgative, consisting of anhydrous magnesium sulfate, potassium sulfate, anhydrous sodium sulfate, and simethicone, the tablet being manufactured into a preparation without adding a lubricant.

2. The tablet according to claim 1, wherein water is added in an amount of 0.1 to 2.0 wt. % with respect to the total weight of an uncoated tablet in the manufacture of the tablet.

3. The tablet for oral application according to claim 1, being manufactured by a direct tableting.

* * * * *